United States Patent
Kawai et al.

(10) Patent No.: US 6,746,492 B2
(45) Date of Patent: Jun. 8, 2004

(54) SEMIPERMANENT HAIR DYE COMPOSITION

(75) Inventors: Tetsuya Kawai, Tokyo (JP); Takashi Itou, Tokyo (JP)

(73) Assignee: Kao Corporation, Tokyo (JP)

( * ) Notice: Subject to any disclaimer, the term of this patent is extended or adjusted under 35 U.S.C. 154(b) by 151 days.

(21) Appl. No.: 10/022,425

(22) Filed: Dec. 20, 2001

(65) Prior Publication Data

US 2002/0144356 A1 Oct. 10, 2002

(30) Foreign Application Priority Data

Jan. 5, 2001 (JP) ........................................ 2001-000465

(51) Int. Cl.[7] ................................................ A61K 7/13
(52) U.S. Cl. ........................ 8/405; 8/407; 8/414; 8/426; 8/435; 8/454; 8/455; 8/462; 8/463; 8/466; 8/578; 8/581; 8/632; 8/678
(58) Field of Search ............................ 8/405, 407, 414, 8/426, 435, 454, 455, 462, 463, 466, 578, 581, 632, 678

(56) References Cited

U.S. PATENT DOCUMENTS

| | | | | |
|---|---|---|---|---|
| 5,332,581 A | * | 7/1994 | Yoshihara et al. | ............. 424/70 |
| 6,071,504 A | * | 6/2000 | Kawai et al. | ............. 424/70.12 |
| 6,197,911 B1 | * | 3/2001 | Richard et al. | ................ 528/15 |
| 6,240,929 B1 | * | 6/2001 | Richard et al. | ............. 132/202 |

* cited by examiner

*Primary Examiner*—Brian P. Mruk
*Assistant Examiner*—Eisa Elhilo
(74) *Attorney, Agent, or Firm*—Oblon, Spivak, McClelland, Maier & Neustadt, P.C.

(57) ABSTRACT

A semipermanent hair dye composition comprising (A) a direct dye, (B) a hydrocarbon oil and (C) polyoxyalkylene-modified dimethyl polysiloxane.

The semipermanent hair dye composition can uniformly dye hair without coloring the scalp and skin and gives the hair an excellent feel after hair coloring.

29 Claims, No Drawings

SEMIPERMANENT HAIR DYE COMPOSITION

BACKGROUND OF THE INVENTION

1. Field of the Invention

The present invention relates to a semipermanent hair dye composition which can uniformly dye hair without coloring the scalp and skin and gives the hair an excellent feel after hair coloring.

2. Description of the Background Art

Semipermanent hair dye compositions that a direct dye is caused to penetrate into hair to color the hair have been known as hair dye compositions. Since the direct dye is great in molecular size, it can not easily penetrate into hair, and so it has involved a problem that it takes a long time to color the hair with such a dye. However, the treatment time is greatly shortened at present with the development of the penetration-enhancing technique with solvents.

However, the skin is colored with more ease than the hair due to the difference in structure between them. Therefore, when a treatment is conducted with a hair dye composition using a direct dye, such a composition has involved a problem that it colors the surface of the scalp at the same time as hair coloring.

Therefore, there has been a demand for development of a semipermanent hair dye composition which can uniformly dye hair without coloring the scalp and skin and gives the hair an excellent feel after hair coloring.

SUMMARY OF THE INVENTION

The present inventors have found that a hydrocarbon oil and polyoxyalkylene-modified dimethyl polysiloxane are used in combination with a direct dye, the above problem can be solved.

According to the present invention, there is thus provided a semipermanent hair dye composition comprising the following components (A), (B) and (C):

(A) a direct dye;
(B) a hydrocarbon oil; and
(C) polyoxyalkylene-modified dimethyl polysiloxane.

The hair dye composition according to the present invention can uniformly dye hair without coloring the scalp and skin and gives the hair a moisturized and smooth feel after hair coloring.

DETAILED DESCRIPTION OF THE PREFERRED EMBODIMENTS

Examples of the direct dye of the component (A) include nitro dyes, anthraquinone dyes and acid dyes, oil-soluble dyes and basic dyes.

Examples of the nitro dyes include 3,4-diaminonitrobenzene, 2,5-diaminonitrobenzene, 2-amino-5-N-β-hydroxyethylaminonitrobenzene, 2-N-β-hydroxyethylamino-5-N,N-bis-β-hydroxyethylaminonitrobenzene, 2-N-methylamino-5-N,N-bis(β-hydroxy-ethyl)aminonitrobenzene, 2-N-methylamino-5-N-methyl-β-hydroxyethylaminonitrobenzene, 2-N-β-hydroxy-ethylamino-5-hydroxynitrobenzene, 3-methoxy-4-N-β-hydroxyethylaminonitrobenzene, 4-nitro-3-methylaminophenoxyethanol, 2-N-β-hydroxyethylamino-5-aminonitrobenzene, 2-N-β-hydroxyethylamino-nitrobenzene, 3-amino-4-N-β-hydroxyethylaminonitrobenzene, 3-β-hydroxyethoxy-4-N-β-hydroxyethylaminonitrobenzene, 2-amino-5-N-methylaminonitrobenzene, 2-amino-3-methylnitrobenzene, 2-N-β-hydroxyethylamino-5-β,γ-dihydroxypropoxynitrobenzene, 3-hydroxy-4-N-β-hydroxyethylaminonitrobenzene, 3-hydroxy-4-aminonitrobenzene, 2,5-N,N'-β-hydroxyethylaminonitrobenzene, 2-N-methylamino-4-o-β,γ-dihydroxypropoxynitrobenzene, 2-N-β-aminoethylamino-5-N,N-bis(β-hydroxyethyl)aminonitrobenzene, 2-N-β-aminoethylamino-4-methoxynitrobenzene and 2-N-β-aminoethylamino-5-β-hydroxyethoxynitrobenzene.

Examples of the anthraquinone dyes include 1-amino-4-methylaminoanthraquinone and 1,4-diaminoanthraquinone.

Examples of the acid dyes include Acid Red 27, Acid Red 51, Acid Red 18, Acid Red 92, Acid Red 94, Acid Red 52, Pigment Red 57-1, Acid Red 33, Acid Red 87, Acid Violet 9, Food Red 6, Acid Red 26, Food Red 1, Acid Red 88, Acid Orange 7, Acid Red 95, Acid Yellow 23, Food Yellow 3, Acid Yellow 73, Acid Yellow 3, Acid Yellow 40, Acid Yellow 1, Acid Yellow 36, Acid Yellow 11, Food Green 3, Acid Green 25, Solvent Green 7, Acid Green 5, Acid Green 1, Acid Green 3, Food Blue 2, Acid Blue 74, Acid Blue 5, Acid Blue 9, Acid Violet 43, Acid Black 1, Acid Blue 1, Acid Blue 3, Acid Blue 62, Acid Black 52, Acid Brown 13, Acid Green 50, Acid Orange 6, Acid Red 14, Acid Red 35, Acid Red 73, Acid Red 184 and Brilliant Black 1.

Examples of the oil-soluble dyes include Solvent Red 49, Solvent Red 48, Solvent Red 23, Solvent Red 72, Solvent Red 73, Acid yellow 33, Solvent Green 3, Solvent Violet 13, Solvent Red 24, Solvent Orange 7, Solvent Orange 2, Solvent Yellow 5, Solvent Yellow 6 and Solvent Blue 63.

Examples of the basic dyes include Basic Blue 6, Basic Blue 7, Basic Blue 9, Basic Blue 26, Basic Blue 41, Basic Blue 99, Basic Brown 4, Basic Brown 16, Basic Brown 17, Basic Green 1, Basic Red 2, Basic Red 12, Basic Red 22, Basic Red 51, Basic Red 76, Basic Violet 1, Basic Violet 3, Basic Violet 10, Basic Violet 14, Basic Violet 57, Basic Yellow 87 and Basic Orange 31.

Among these, the acid dyes are preferred, with Acid Yellow 23, Acid Yellow 1, Acid Orange 7, Food Green 3, Acid Green 25, Solvent Green 7, Acid Red 27, Acid Red 92, Acid Red 52, Pigment Red 57-1, Acid Red 33, Food Blue 2, Acid Blue 9, Acid Violet 43 and Acid Black 1 being particularly preferred.

The above-described direct dyes may also be used in any combination thereof, and the content thereof is preferably 0.005 to 5% by weight, particularly 0.01 to 2% by weight in the dye composition according to the present invention.

Examples of the hydrocarbon oil of the component (B) include liquid paraffin, liquid isoparaffin and squalane. The hydrocarbon oils may also be used in any combination thereof, and the content thereof is preferably 0.1 to 20% by weight, more preferably 0.5 to 10% by weight, particularly 1 to 5% by weight in the dye composition according to the present invention from the viewpoints of the inhibitory effect on coloring of the scalp and skin and giving no sticky feel.

The polyoxyalkylene-modified dimethyl polysiloxane of the component (C) is that with a polyoxyalkylene group, preferably a polyoxyethylene group bonded to a main chain of dimethyl polysiloxane, and those having HLB of 1 to 6, particularly 2 to 5 are preferred. Such a polysiloxane may have a polyoxypropylene group in addition to the polyoxyethylene group. Specific examples thereof include Silicone KF6015, KF6017, KF945A and KF353A, KF352A (all, products of Shin-Etsu Chemical Co., Ltd.), SILWET L-720, L-7001 and L-7002 (all, products of Nippon Unicar Co., Ltd.), and Silicone SH-3775 (product of Toray Dow Corning Co., Ltd.). The polyoxyalkylene-modified dimethyl polysiloxanes may also be used in any combination thereof, and the content thereof is preferably 0.001 to 30% by weight, more preferably 0.01 to 10% by weight, particularly 0.1 to 5% by weight in the dye composition according to the present invention from the viewpoints of a feel upon application, stability of the system and rinsing out.

In order to facilitate penetration of a direct dye into hair to improve hair-dyeing ability, an organic solvent selected from a compound represented by the following general formula (1), a compound represented by the following general formula (2), an alkylene carbonate having 2 to 5 carbon atoms and a 5- or 6-membered cyclic lactone which may be substituted by an alkyl, alkenyl, alkoxy or acyl group is preferably contained as a component (D) in the hair dye compositions according to the present invention.

$$R^1-(OCH_2CH_2)_p-(OCH_2CH)_q-Z \atop \underset{(CH_2)_r-Y}{|}$$ (1)

wherein $R^1$ is a hydrogen atom, a low alkyl group or a group represented by the following formula:

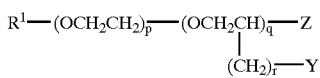

in which $R^2$ is a hydrogen atom, or a methyl or ethyl group, and $R^3$ is a single bone or a saturated or unsaturated hydrocarbon group having 1 to 3 carbon atoms, Y and Z are, independently of each other, a hydrogen atom or a hydroxyl group, and p, q and r are, independently of each other, an integer of 0 to 5, with the proviso that the cases where p and q are 0, and Z is a hydrogen atom, and where p and q are 0, $R^1$ is a hydrogen atom, and Z is a hydroxyl group are excluded.

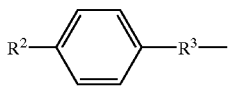 (2)

wherein $R^4$ is a linear or branched alkyl group having 1 to 18 carbon atoms.

Specific examples of the organic solvent of the component (D) include ethanol, 1-propanol, 2-propanol, 1-butanol, isobutanol, ethylene glycol, propylene glycol, benzyl alcohol, cinnamyl alcohol, phenethyl alcohol, p-anisyl alcohol, p-methylbenzyl alcohol, phenoxyethanol, 2-benzyloxyethanol, methylcarbitol, ethylcarbitol, propylcarbitol, butylcarbitol, triethylene glycol monoethyl ether, triethylene glycol monobutyl ether, glycerol, N-methylpyrrolidone, N-octylpyrrolidone, N-laurylpyrrolidone, ethylene carbonate, propylene carbonate, γ-butyrolactone, γ-pentanolactone, δ-pentanolactone, γ-hexanolactone, δ-hexanolactone, γ-heptanolactone, δ-heptanolactone, γ-octanoic lactone and α-methyl-γ-butyrolactone.

These organic solvents of the component (D) may also be use in any combination thereof, and are preferably contained in a proportion of 0.1 to 50% by weight, more preferably 1 to 30% by weight, particularly 5 to 20% by weight in the dye composition according to the present invention.

In the dye compositions according to the present invention, an anionic or nonionic water-soluble polymer may preferably be incorporated as a component (E) for the purpose of improving stability and usability as a composition, such as easy spreading upon application. Examples of the anionic polymer include xanthan gum, hydroxypropyl xanthan gum, Welan gum, Gellan gum, carboxyvinyl polymer, guar gum, acrylic acid-methacrylic ester copolymers and partially crosslinked products of methyl vinyl ether-maleic anhydride copolymers with 1,9-decadiene. Examples of the nonionic polymer include polyethylene glycol, hydroxyethyl cellulose, polyvinyl pyrrolidone and polyvinyl pyrrolidone-vinyl acetate copolymers. Xanthan gum and hydroxypropyl xanthan gum are particularly preferred. These water-soluble polymers of the component (E) may be used in any combination thereof, and preferably contained in a proportion of 0.01 to 10% by weight, more preferably 0.1 to 5% by weight, particularly 0.5 to 3% by weight in the hair dye composition according to the present invention.

Taking the case where an acid dye is used as the direct dye of the component (A) as an example, the pH of the hair dye composition according to the present invention is preferably within a range of 2 to 5, more preferably 2 to 4.5, particularly 2.5 to 4 when it is diluted to 1/10 with water from the viewpoints of even hair coloring and inhibition of irritation to the hand and skin. As a pH adjuster, may be used an organic acid, inorganic acid or a salt thereof, with an organic acid or a salt thereof being particularly preferred. Examples of the organic acid include citric acid, glycolic acid, succinic acid, tartaric acid, lactic acid, fumaric acid, malic acid, leveling acid, butyric acid and oxalic acid. Examples of the inorganic acid include phosphoric acid sulfuric acid and nitric acid. Examples of the salts thereof include sodium salts, potassium salts, ammonium salts and alkanolamine salts (for example, triethanolamine salts). The pH adjusters may also be used in any combination thereof and are preferably used in a proportion of 0.01 to 10% by weight, more preferably 0.1 to 7% by weight, particularly 1 to 5% by weight.

In order to enhance the conditioning effect on hair, an ester oil, another silicone derivative than the component (C), a higher alcohol, an fatty acid or the like may be contained in the hair dye compositions according to the present invention. Examples of the ester oil include isopropyl palmitate, isopropyl myristate and glyceryl laurate. Examples of the silicone derivative include dimethyl polysiloxane, methylphenyl polysiloxane, amino-modified silicones and alkyl-modified silicones. Examples of the higher alcohol include lauryl alcohol, myristyl alcohol, oleyl alcohol and behenyl alcohol. Examples of the fatty acid include lauric acid, stearic acid, oleic acid and behenic acid. These compounds may also be used in any combination thereof, and the content thereof is preferably 0.1 to 20% by weight, more preferably 0.5 to 10% by weight, particularly 1 to 5% by weight. The hair dye compositions according to the present invention are prepared by blending the above-described respective components with an aqueous medium.

EXAMPLES 1 AND 2, AND COMPARATIVE EXAMPLES 1 TO 5

Hair dye compositions having their corresponding formulations shown in Table 1 were prepared to evaluate them in the following respective methods.

(Evaluation Method)

[Hair-Dyeing Ability] and [Smoothness of Hair After Drying]

Each (2.5 g) of the hair dye compositions shown in Table 1 was applied to tresses (5 g) for evaluation composed of Japanese woman hair about 15 cm long, which had been untreated, and the tresses were then shampooed, rinsed and then dried. With respect to the hair-dyeing ability and smoothness of hair after drying, the hair dye compositions were evaluated by 10 special panelists to rank them in accordance with the following standard. The total scores thereof are shown in Table 1.

Evaluation Standard of [Hair-dyeing Ability]

| | |
|---|---|
| Evenly dyed | 5 points |
| Somewhat unevenly dyed | 3 points |
| Scarcely dyed | 1 point. |

Evaluation Standard of [Smoothness of Hair After Drying]

| | |
|---|---|
| Felt smooth | 5 points |
| Somewhat felt smooth | 3 points |
| Felt creaky | 1 point. |

[Coloring Tendency to Skin]

The skin of an upper arm of Japanese woman was washed with a shampoo, and each (about 0.5 g) of the hair dye compositions shown in Table 1 was put in a circle about 1.0 cm in diameter on the skin. The skin was left to stand for 10 minutes at room temperature, and then washed with water, shampooed and rinsed. With respect to the condition of skin coloring, the hair dye compositions were evaluated by 10 special panelists to rank them in accordance with the following standard. The total scores thereof are shown in Table 1.

Evaluation Standard of [Coloring Tendency to Skin]

| | |
|---|---|
| Not colored at all | 5 points |
| Somewhat colored | 3 points |
| Colored to a considerable extent | 1 point. |

TABLE 1

| | Example | | Comparative Example | | | | | (% by weight) |
|---|---|---|---|---|---|---|---|---|
| | 1 | 2 | 1 | 2 | 3 | 4 | 5 | |
| Acid Red 52 | 0.5 | 0.5 | 0.5 | 0.5 | 0.5 | 0.5 | 0.5 | |
| Propylene carbonate | 20 | — | 20 | 20 | — | — | — | |
| Benzyl alcohol | — | 10 | — | — | 10 | — | — | |
| Ethanol | 5 | 15 | 5 | 5 | 15 | 25 | 5 | |
| Xanthan gum | — | — | — | 2 | — | — | — | |
| Light isoparaffin | 3 | 3 | — | — | — | — | 3 | |
| Polyethylene glycol (Mw 2,000,000) | 0.01 | 0.05 | 0.01 | — | 0.05 | 0.05 | — | |
| Polyoxyalkylene-modified dimethyl polysiloxane *1 | 2 | 2 | 2 | — | 2 | 2 | — | |
| Lactic acid (90%) | | | | 5 | | | | |
| Sodium hydroxide | | | Adjusted to pH3 (when diluted to 1/10) | | | | | |
| Perfume base | | | 0.1 | | | | | |

TABLE 1-continued

| | Example | | Comparative Example | | | | | (% by weight) |
|---|---|---|---|---|---|---|---|---|
| | 1 | 2 | 1 | 2 | 3 | 4 | 5 | |
| Purified water | | | Balance | | | | | |
| Evaluation | Hair-dyeing ability | 50 | 50 | 50 | 50 | 50 | 32 | 20 |
| | Coloring tendency to skin | 48 | 44 | 24 | 22 | 16 | 30 | 28 |
| | Smoothness of hair | 46 | 48 | 32 | 18 | 36 | 40 | 24 |

*1 Silicone KF6017 (product of Shin-Etsu Chemical Co., Ltd.)

Both hair dye compositions according to the present invention shown above were good in hair-dyeing ability and feel and scarcely observed coloring the skin.

EXAMPLE 3

| | (% by weight) |
|---|---|
| Acid Orange 7 | 0.4 |
| Acid Black 1 | 0.2 |
| Acid Violet 1 | 0.1 |
| Ethanol | 5.0 |
| Propylene carbonate | 10.0 |
| Benzyloxyethanol | 10.0 |
| Partially crosslinked product of Methyl vinyl ether/maleic anhydride Copolymer with 1,9-decadiene | 3.0 |
| Light isoparaffin | 3.0 |
| Polyethylene glycol (Mw: 2,000,000) | 0.03 |
| Polyethylene glycol (Mw: 20,000) | 1.0 |
| Polyoxyalkylene-modified dimethyl * Polysiloxane | 2.0 |
| Lactic acid (90%) | 5.0 |
| Sodium hydroxide | Adjusted to pH 3 (when diluted to 1/10) |
| Perfume base | 3.0 |
| Purified water | Balance |
| Total | 100.0 |

* Silicone KF6017 (product of Shin-Etsu Chemical Co., Ltd.)

EXAMPLE 4

| | (% by weight) |
|---|---|
| Acid Orange 7 | 0.4 |
| Acid Black 1 | 0.2 |
| Acid Violet 43 | 0.1 |
| Ethanol | 5.0 |
| Propylene carbonate | 10.0 |
| Benzyloxyethanol | 10.0 |
| N-Methylpyrrolidone | 3.0 |
| Partially crosslinked product of Methyl vinyl ether/maleic anhydride Copolymer with 1,9-decadiene | 3.0 |
| Light isoparaffin | 3.0 |
| Polyethylene glycol (Mw: 2,000,000) | 0.05 |
| Polyoxyalkylene-modified dimethyl * Polysiloxane | 2.0 |
| Lactic acid (90%) | 5.0 |
| Sodium hydroxide | Adjusted to pH 3 (when diluted to 1/10) |
| Perfume base | 3.0 |
| Purified water | Balance |
| Total | 100.0 |

* Silicone KF945A (product of Shin-Etsu Chemical Co., Ltd.)

EXAMPLE 5

|  | (% by weight) |
|---|---|
| Acid Orange 7 | 0.4 |
| Acid Black 1 | 0.2 |
| Acid Violet 43 | 0.1 |
| Ethanol | 5.0 |
| Propylene carbonate | 10.0 |
| Benzyloxyethanol | 10.0 |
| Welan Gum | 2.0 |
| Light isoparaffin | 3.0 |
| Polyethylene glycol (Mw: 2,000,000) | 3.0 |
| Polyoxyalkylene-modified dimethyl * Polysiloxane | 2.0 |
| Citric acid | 4.0 |
| Sodium hydroxide | Adjusted to pH 3 (when diluted to 1/10) |
| Perfume base | 3.0 |
| Purified water | Balance |
| Total | 100.0 |

* Silicone KF6O17 (product of Shin-Etsu Chemical Co., Ltd.)

EXAMPLE 6

|  | (% by weight) |
|---|---|
| Acid Orange 7 | 0.4 |
| Acid Black 1 | 0.2 |
| Acid Violet 43 | 0.1 |
| Ethanol | 5.0 |
| Benzyloxyethanol | 3.0 |
| γ-Hexanolactone | 10.0 |
| Partially crosslinked product of Methyl vinyl ether/maleic anhydride Copolymer with 1,9-decadiene | 3.0 |
| Light isoparaffin | 3.0 |
| Polyethylene glycol (Mw: 2,000,000) | 0.05 |
| Polyoxyalkylene-modified dimethyl * Polysiloxane | 2.0 |
| Lactic acid (90%) | 5.0 |
| Sodium hydroxide | Adjusted to pH 3 (when diluted to 1/10) |
| Perfume base | 3.0 |
| Purified water | Balance |
| Total | 100.0 |

* Silicone KF945A (product of Shin-Etsu Chemical Co., Ltd.)

What is claimed is:

1. A semipermanent hair dye composition comprising the following components (A), (B), and (C):

(A) at least one acid dye;
   (B) at least one hydrocarbon oil; and
   (C) at least one polyoxyalkylene-modified dimethyl polysiloxane,
   wherein the pH of the hair dye composition is within a range of 2 to 5 when it is diluted to 1/10-strength with water.

2. The semipermanent hair dye composition according to claim 1, which further comprises:

(D) at least one organic solvent selected from a compound represented by the following general formula (1):

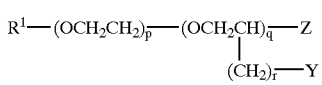

wherein $R^1$ is a hydrogen atom, a low alkyl group or a group represented by the following formula:

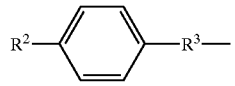

in which $R^2$ is a hydrogen atom, or a methyl or ethyl group, and $R^3$ is a single bond or a saturated or unsaturated hydrocarbon group having 1 to 3 carbon atoms, Y and Z are, independently of each other, a hydrogen atom or a hydroxyl group, and P, q and r are, independently of each other, an integer of 0 to 5, with the proviso that the cases where p and q are 0, and Z is a hydrogen atom, and where p and q are 0, $R^1$ is a hydrogen atom, and Z is a hydroxyl group are excluded, a compound represented by the following general formula (2):

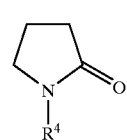

wherein $R^4$ is a linear or branched alkyl group having 1 to 18 carbon atoms, an alkylene carbonate having 2 to 5 carbon atoms and a 5- or 6-membered cyclic lactone which may be substituted by an alkyl, alkenyl, alkoxy or acyl group.

3. The semipermanent hair dye composition according to claim 1, wherein said acid dye is selected from the group consisting of Acid Red 27, Acid Red 51, Acid Red 18, Acid Red 92, Acid Red 94, Acid Red 52, Pigment Red 57-1, Acid Red 33, Acid Red 87, Acid Violet 9, Food Red 6, Acid Red 26, Food Red 1, Acid Red 88, Acid Orange 7, Acid Red 95, Acid Yellow 23, Food Yellow 3, Acid Yellow 73, Acid Yellow 3, Acid Yellow 40, Acid Yellow 1, Acid Yellow 36, Acid Yellow 11, Food Green 3, Acid Green 25, Solvent Green 7, Acid Green 5, Acid Green 1, Acid Green 3, Food Blue 2, Acid Blue 74, Acid Blue 5, Acid Blue 9, Acid Violet 43, Acid Black 1, Acid Blue 1, Acid Blue 3, Acid Blue 62, Acid Black 52, Acid Brown 13, Acid Green 50, Acid Orange 6, Acid Red 14, Acid Red 35, Acid Red 73, Acid Red 184, and Brilliant Black 1.

4. The semipermanent hair dye composition according to claim 1, wherein said acid dye is selected from the group consisting of Acid Yellow 23, Acid Yellow 1, Acid Orange 7, Food Green 3, Acid Green 25, Solvent Green 7, Acid Red 27, Acid Red 92, Acid Red 52, Pigment Red 57-1, Acid Red 33, Food Blue 2, Acid Blue 9, Acid Violet 43, and Acid Black 1.

5. The semipermanent hair dye composition according to claim 1, wherein said at least one acid dye is at a concentration ranging from 0.005 to 5% by weight.

6. The semipermanent hair dye composition according to claim 5, wherein said at least one acid dye is at a concentration ranging from 0.01 to 2% by weight.

7. The semipermanent hair dye composition according to claim 1, wherein said hydrocarbon oil is selected from the group consisting of liquid paraffin, liquid isoparaffin, and squalane.

8. The semipermanent hair dye composition according to claim 1, wherein said at least one hydrocarbon oil is at a concentration ranging from 0.1 to 20% by weight.

9. The semipermanent hair dye composition according to claim 8, wherein said at least one hydrocarbon oil is at a concentration ranging from 0.5 to 10% by weight.

10. The semipermanent hair dye composition according to claim 8, wherein said at least one hydrocarbon oil is at a concentration ranging from 1 to 5% by weight.

11. The semipermanent hair dye composition according to claim 1, wherein said polyoxyalkylene-modified dimethyl polysiloxane has a polyoxyalkylene group bonded to a main chain of dimethyl polysiloxane.

12. The semipermanent hair dye composition according to claim 11, wherein said polyoxyalkylene group is selected from the group consisting of polyoxyethylene and polyoxypropylene.

13. The semipermanent hair dye composition according to claim 1, wherein said polyoxyalkylene-modified dimethyl polysiloxane has a HLB of 1 to 6.

14. The semipermanent hair dye composition according to claim 1, wherein said at least one polyoxyalkylene-modified dimethyl polysiloxane is at a concentration ranging from 0.001 to 30% by weight.

15. The semipermanent hair dye composition according to claim 14, wherein said at least one polyoxyalkylene-modified dimethyl polysiloxane is at a concentration ranging from 0.01 to 10% by weight.

16. The semipermanent hair dye composition according to claim 14, wherein said at least one polyoxyalkylene-modified dimethyl polysiloxane is at a concentration ranging from 0.1 to 5% by weight.

17. The semipermanent hair dye composition according to claim 2, wherein said organic solvent is a compound represented by general formula (1).

18. The semipermanent hair dye composition according to claim 2, wherein said organic solvent is a compound represented by general formula (2).

19. The semipermanent hair dye composition according to claim 2, wherein said organic solvent is an alkylene carbonate having 2 to 5 carbon atoms.

20. The semipermanent hair dye composition according to claim 2, wherein said organic solvent is a 5- or 6-membered cyclic lactone which may be substituted by an alkyl, alkenyl, alkoxy or acyl group.

21. The semipermanent hair dye composition according to claim 2, wherein said at least one organic solvent is at a concentration of 0.1 to 50% by weight.

22. The semipermanent hair dye composition according to claim 1, further comprising:

(E) at least one anionic or nonionic water-soluble polymer.

23. The semipermanent hair dye composition according to claim 22, wherein said at least one anionic or nonionic water-soluble polymer is present at a concentration of 0.01 to 10% by weight.

24. The semipermanent hair dye composition according to claim 2, further comprising:

(E) an anionic or nonionic water-soluble polymer.

25. The semipermanent hair dye composition according to claim 24, wherein said anionic or nonionic water-soluble polymer is present at a concentration of 0.01 to 10% by weight.

26. The semipermanent hair dye composition according to claim 1, wherein said pH is adjusted by use of a pH adjuster selected from the group consisting of an organic acid, an inorganic acid, a salt of an organic acid, and a salt of an inorganic acid.

27. The semipermanent hair dye composition according to claim 26, wherein said pH adjuster is present at a concentration of 0.01 to 10% by weight.

28. The semipermanent hair dye composition according to claim 1, wherein said composition further comprises at least one additive selected from the group consisting of an ester oil, a silicone derivative other than component (C), a higher alcohol, and a fatty acid.

29. The semipermanent hair dye composition according to claim 28, wherein said at least one additive is present at a concentration of 0.1 to 20% by weight.

* * * * *